US006849047B2

(12) United States Patent
Goodwin

(10) Patent No.: US 6,849,047 B2
(45) Date of Patent: Feb. 1, 2005

(54) INTRAOSTEAL ULTRASOUND DURING SURGICAL IMPLANTATION

(75) Inventor: Mark R. Goodwin, Gilbertsville, PA (US)

(73) Assignee: Cutting Edge Surgical, Inc., Gilbertsville, PA (US)

(*) Notice: Subject to any disclaimer, the term of this patent is extended or adjusted under 35 U.S.C. 154(b) by 0 days.

(21) Appl. No.: 10/403,326

(22) Filed: Mar. 28, 2003

(65) Prior Publication Data

US 2003/0187348 A1 Oct. 2, 2003

Related U.S. Application Data

(62) Division of application No. 10/280,305, filed on Oct. 24, 2002, now Pat. No. 6,579,244.
(60) Provisional application No. 60/348,446, filed on Oct. 24, 2001.

(51) Int. Cl.[7] .................................................. A61B 8/00
(52) U.S. Cl. ....................................................... 600/437
(58) Field of Search ................................. 600/437–471, 600/407, 561, 587, 559; 606/53–105.5; 514/365; 623/17.16; 604/22; 310/334

(56) References Cited

U.S. PATENT DOCUMENTS

| | | | |
|---|---|---|---|
| 4,809,689 A | | 3/1989 | Anapliotis |
| 4,936,848 A | * | 6/1990 | Bagby ...................... 623/17.16 |
| 4,979,939 A | | 12/1990 | Shiber |
| 5,188,111 A | * | 2/1993 | Yates et al. .................. 600/434 |
| 5,235,981 A | * | 8/1993 | Hascoet et al. .............. 600/437 |
| 5,309,898 A | | 5/1994 | Kaufman et al. |
| 5,456,686 A | * | 10/1995 | Klapper et al. ................ 606/99 |
| 5,785,041 A | * | 7/1998 | Weinstein et al. ........... 600/407 |
| 5,957,847 A | * | 9/1999 | Minakuchi et al. .......... 600/449 |
| 6,205,411 B1 | | 3/2001 | DiGioia, III et al. |
| 6,432,058 B1 | * | 8/2002 | Sloth .......................... 600/462 |
| 6,495,579 B1 | * | 12/2002 | Hunter ........................ 514/365 |
| 6,579,244 B2 | * | 6/2003 | Goodwin ..................... 600/561 |
| 6,607,487 B2 | * | 8/2003 | Chang et al. ................ 600/437 |

FOREIGN PATENT DOCUMENTS

| JP | 08-137006 | * | 5/1996 |
|---|---|---|---|

* cited by examiner

*Primary Examiner*—Francis J. Jaworski
(74) *Attorney, Agent, or Firm*—Pabst Patent Group LLP

(57) ABSTRACT

IntraOsteal UltraSound (IOUS) is the use of acoustical energy to facilitate "real-time" manipulation and navigation of a device for intraosseous placement of synthetic or biologic implants and to diagnose the condition of the tissue into which the implant is being placed. Representative applications include placement of synthetic or biologic implants, such as bone screws, through vertebral pedicles during spinal fusion surgery. Devices for use in the placement of the implants include a means for creating a lumen or channel into the bone at the desired site in combination with a probe for providing realtime feedback of differences in density of the tissue, typically differences in acoustical impedance between cancellous and cortical bone. The devices will also typically include means for monitoring the feedback such as a screen creating an image for the surgeon as he creates the channel, and/or an audible signal which different tissues are present. The system can also be used for diagnostic applications.

6 Claims, 4 Drawing Sheets

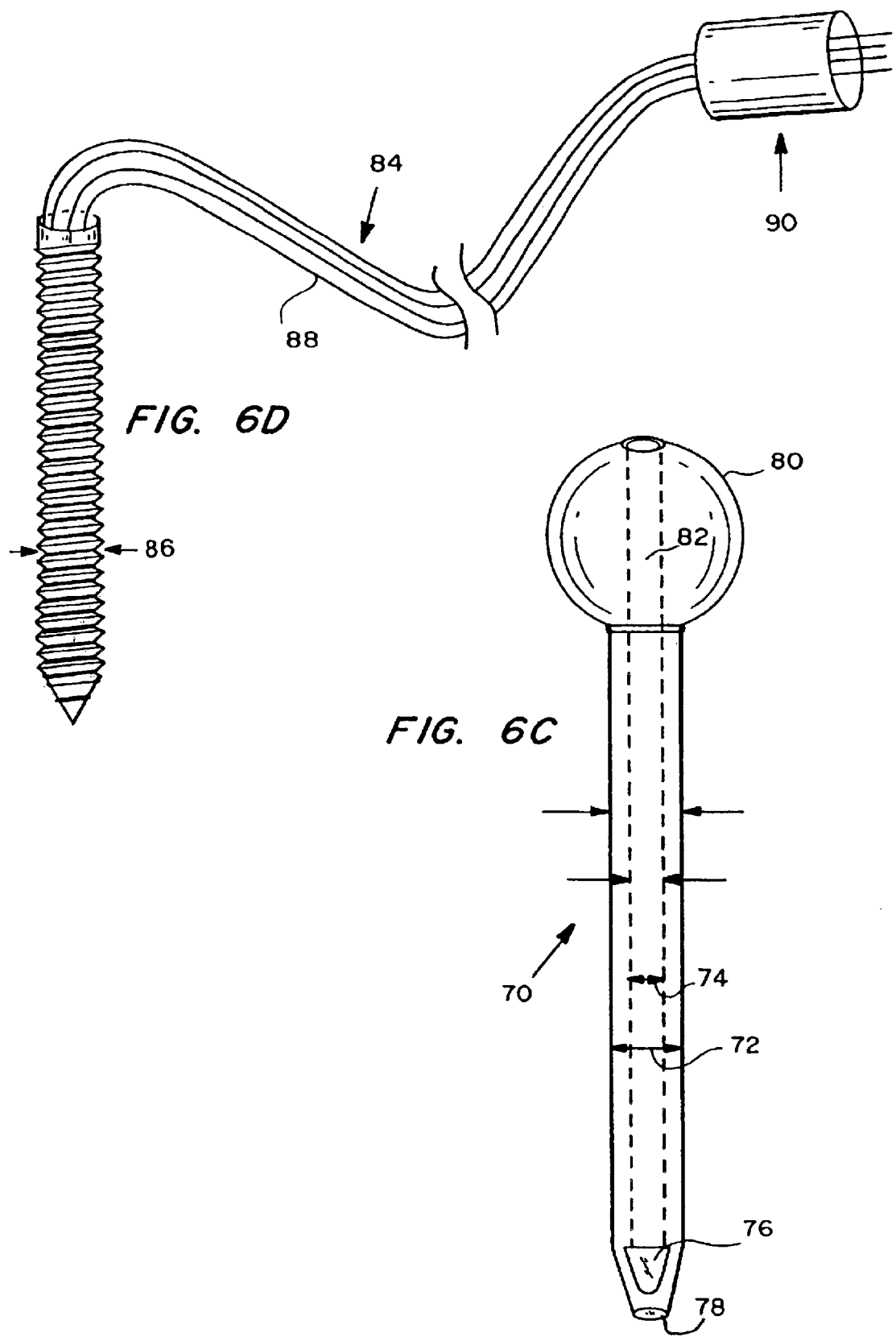

INTRAOSTEAL ULTRASOUND DURING SURGICAL IMPLANTATION

This application is a divisional of U.S. Ser. No. 10,280,305 filed Oct. 24, 2002 by Mark R. Goodwin, entitled "*Intraoseal Ultrasound During Surgical Implantation*", now U.S. Pat. No. 6,579,244 which claims priority to U.S. Provisional Patent Application No. 60/348,446 filed Oct. 24, 2001.

BACKGROUND OF THE INVENTION

The present invention is generally in the field of methods and devices for surgical placement of implants, especially into bone.

Surgical implantation of devices such as screws, pins, and other medical implants into bone is frequently the only means to safely immobilize the bone. Typically, this is done by passing a probe through the cortical bone, the dense, hard bone on the outside of bony structures, and into the cancellous bone, the soft, compliant spongy bone on the inside of the bone.

As shown in FIG. 1, the relevant structures are the pedicles 12 and vertebral body 10. These structures are comprised of two types of bone: cortical 14 and cancellous 16. Cortical bone is the dense, hard bone covering the illustrated structures. Cancellous bone, commonly referred to as "spongy bone" is "soft" and compliant and provides the inner core for these structures.

Surgeons exploit the difference in these two bone types during pedicular cannulation. When passing a blunt, narrow "probe" through the pedicle, the instrument tip tends to follow the path of least resistance, the cancellous bone. The operator continues to direct this instrument, usually with x-ray assistance, until it has penetrated 50–80% of the anterior/posterior diameter of vertebral body. Successful cannulation is achieved when an intra-cancellous pilot channel is created without a breach of the cortical bone. A breach can injure critical structures in close proximity, such as spinal cord, nerve root, and vessels. The larger the cancellous inner core and the thicker the outer cortex, the easier the task. This is the case, for example, in the lumbar vertebrae, particularly the L3-S1 pedicles. However, in ascending the spine from the lumbar to thoracic and cervical vertebrae, the complexity of the task increases substantially. Since pedicular cannulation is essentially a "blind" technique, tactile feedback is critical to the operator during creation of the pilot channel. When the boundaries of the bone type are large and well defined, as they generally are in the lumbar pedicles, the relatively thick cortical wall and large core of cancellous bone facilitates intraosteal passage of a blunt tipped probe. The cortical/cancellous boundary is readily detected as the probe is advanced. In higher vertebrae, i.e., thoracic and cervical, the pedicle dimensions decrease markedly. As the overall cross-sectional diameter of the pedicle decreases, so does the cortical wall thickness. As the operator's tactile sensitivity to the cortical/cancellous boundary decreases, the risk for breach increases, even with adjunctive virtual image guidance.

A high complication rate associated with pedicle screw placement in lumbar vertebrae is well documented. As previously stated, the risk is even higher in thoracic and cervical spine. Placement of pedicle screws in the certical vertebrae, with the exception of perhaps C2 and C7, is virtually unheard of. Most posterior fixation procedures of the cervical spine, therefore, are through screw fixation in the lateral masses; not nearly as strong as pedicular fixation.

Since pedicular fixation in many cases provides for maximum construct stability and strength an alternative and improved method and mode of navigation is essential for routine cannulation of these upper vertebral pedicles.

Currently, there is no simple or reliable method to navigate cannulation of vertebral pedicles in vivo and in real time during placement of implants. This is a challenging task even in the hands of the most experienced spine surgeon, especially in the upper thoracic and cervical vertebrae. Current modes of virtual guidance are all based on "historical" data and the images upon which the guidance is dependent do not necessarily present the actual anatomic position at any given instant in real time an instrument is engaging tissue.

It is therefore an object of the present invention to provide methods and devices to guide cannulation or other procedures within bone or similar types of materials in the body, which are reliable and realtime.

SUMMARY OF THE INVENTION

As defined herein, IntraOsteal UltraSound (IOUS) is the use of acoustical energy, i.e., ultrasound, to facilitate "realtime" manipulation and navigation of a device for intraosseous placement of synthetic or biologic implants. Representative applications include placement of synthetic or biologic implants, such as bone screws, through vertebral pedicles during spinal fusion surgery. Such implants are part of a larger "construct" designed to immobilize unstable vertebrae incorporated by it. The purpose of such a construct is to permit bony fusion of those unstable vertebrae that contribute to pain or impaired spine function. Devices for use in the placement of the implants include a means for creating a lumen or channel into the bone at the desired site in combination with a probe for providing realtime feedback of differences in density of the tissue, typically differences in density between cancellous and cortical bone. The devices also typically includes means for monitoring the feedback such as a screen creating an image for the surgeon as he creates the channel.

IOUS can also be used for measurement of bone thickness, identification and confirmation of pseudoarthrosis in failed spinal fusions, bone-to-avascular-necrosis interface, guidance of pedicle screws across a vertebral body during anterior spinal deformity corrective surgery, and search for osteoid osteoma and vascular lesions such as aneurismal bone cysts, etc.

BRIEF DESCRIPTION OF THE DRAWINGS

FIG. 2a, perspective view; FIG. 2b, side view; FIG. 2c, top view.

FIGS. 6a–d are perspective views of the instruments used in the process. FIGS. 6a and 6b are drill bits of a type currently available modified to incorporate transducers that provide feedback to create an image as the drill bit creates a pilot hole. FIGS. 6c and 6d are perspective views of an instrument that is both a transducer and capable of creating a pilot hole.

DETAILED DESCRIPTION OF THE INVENTION

Figure 1:
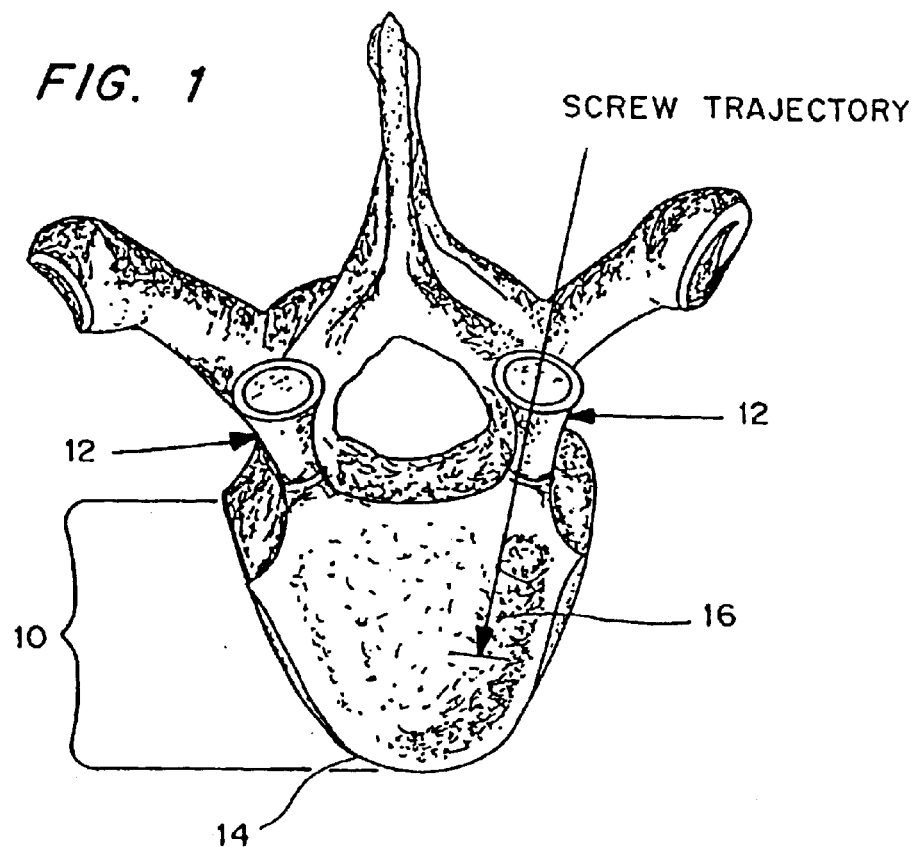
FIG. 1 is a diagram of a thoracic vertebrate (T6) showing the pedicles, cortical bone, cancellous bone, and bone screw trajectory for spinal fusion.

An IntraOsteal UltraSound (IOUS) based system is used for the placement of implants, both initially and/or as the surgeon is operating, and for detection and characterization of bone to enable the surgeon to determine the precise location to begin surgery to place the implant, as well as to determine the condition of the tissues into which the implant is to be placed.

The system includes a device for sensing and alerting via an auditory or visual signal the absence of bone (cortical, cancellous, cartilaginous) i.e., as would be the case of a bony non-union (pseudoarthrosis), fracture, neoplasms, avascular necrosis, vascular lesions, etc. Such abnormalities will have acoustical properties with echogenicity widely disparate from all normal bone types. The IOUS provides a means to qualitatively recognize or delineate abnormal regions, to insure that any implant being guided and placed is done so in bone of a normal caliber (density, homogeneity, architecture, etc.). The frequency range of bone is such that any quantifiable signal falling outside of a particular range will produce an alert signal that is different than that of a signal produced with normal bone. This is important when navigating from one bony structure to another bony structure across a non-bony interface, i.e., as in joints, especially when implanting facet screws, hip pins, etc.

Effective deployment of IOUS can be predicated on a multiple number of factors or variables that are unique to bone, including:

1. Bone mineral density (BMD).
2. Histology of bone;
3. Bone disease or degeneration
4. Water content (blood, bone marrow, etc.).
5. Cartilage composition.

In its totality, bone, in all of its iterations, combinations and architecture has a distinct "signature". Its echogenicity, modes of attenuation, scattering coefficients, and other characteristics will always be quite distinct from other soft tissues. The array of acoustical properties, i.e., frequency, bandwidth, attenuation characteristics, amplitude, scatter coefficients, will all be unique for each type of bone. Effective navigation involves not only delineating cortical bone from cancellous bone but the integrity of those elements as well.

I. Implants

A number of different types of implants can be placed using the devices described herein. In the simplest embodiment, the implant is a titanium screw or pin which is implanted into a channel created by channeling a probe through the cortical bone into the cancellous bone within the bone to be immobilized.

In the preferred embodiment, the bone is a vertebra and channels are created within the pedicles of adjacent vertebrae which are then screwed together. Simply put, this spine construct is analogous to a splint or cast placed on or around long bone fractures until healing (fusion) occurs. Screws can be removed after the bone has healed.

Other implants that can be used include pedicle screws and hip pins. Implants may be formed of metal, ceramic, polymer, biological materials (including bone), and combinations thereof.

II. Devices that can be Used to Image the Area

Devices include at a minimum a probe for moving within the tissue to be imaged and means for applying and/or receiving ultrasound or acoustic energy, and means for transmitting data to an external monitoring means. Optionally, the devices also including means for placement of the implant, and signaling devices that generate a signal when the probe crosses from one type of tissue to another.

Ultrasound is a form of energy that is quantifiable, reliable, non-ionizing, and relatively inexpensive. The different acoustical properties of cortical and cancellous bone make it amenable to real time interrogation and delineation during instrument manipulation. There are two modes by which acoustical energy that is emitted and received in vivo could be utilized for reliable guidance:

1. Visual (Radar): Though a small transducer mounted on or within a narrow instrument, emission of a predefined acoustical signal, can, upon reflection, be electronically processed to present the disparate signals, altered by the marked difference in echogenicity of cortical and cancellous bone, into a visual graphic image displaying the relationship of the instrument tip with respect to the cortical/cancellous tissue in both the axial and sagital planes.

2. Auditory (Sonar): By a process similar to the above, the altered signal can be processed such that when a given threshold is met, e.g., when the instrument tip is in direct contact with cortical bone, an audible tone can be generated alerting the operator of an impending breach if he were to continue the manipulation at the present trajectory.

3. Dual Visual/Auditory: By blending the benefits of both, the operator has constant feedback that would enhance accuracy and efficiency of cannulation.

III. Methods for Detection and Characterization of Bone

The ultrasound is used to measure or provide analysis of one or more factors or variables, including 1. Bone mineral density (BMD);
2. Histology of bone, i.e., cancellous which is trabecular versus cortical which is lamellar;
3. disease such as osteoporosis, calcification, pseudoarthrosis or arthritis;
4. water content (blood, bone marrow, etc.);
5. cartilage composition;
6. lesions, vascular defects, neoplasms, or avascular necrosis.

This information assists in knowing the integrity (ex. normal BMD, low BMD) of where one is going as well as the location (ex. cortical to cancellous) one is going to.

Figures 2A, 2B:
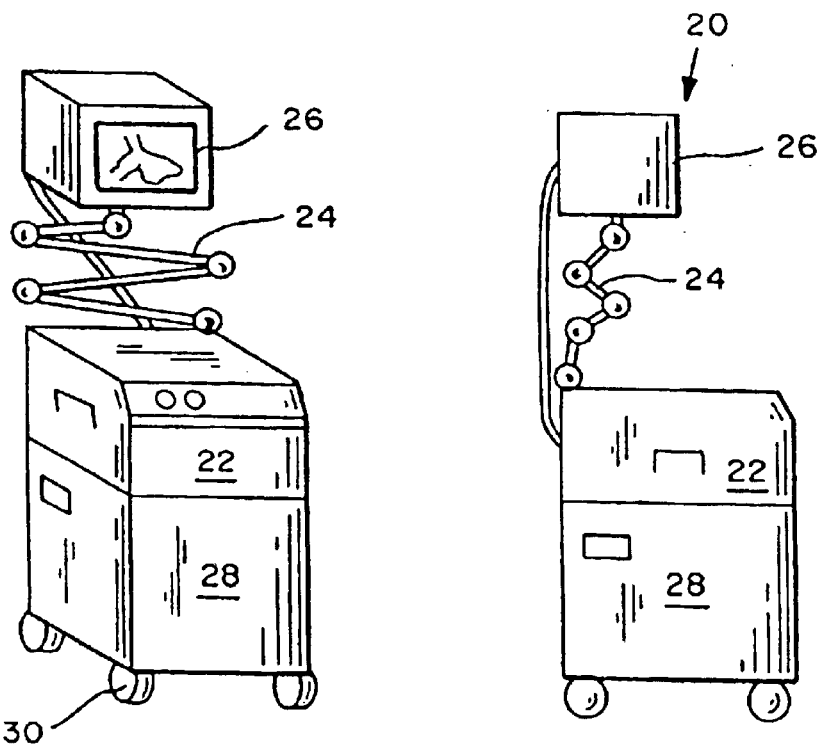
FIGS. 2a, 2b and 2c are diagrams of a device for use in IOUS, including a computer processor, acoustical generator, monitor, articulating arm, and transducer input ports.
Figure 2C:
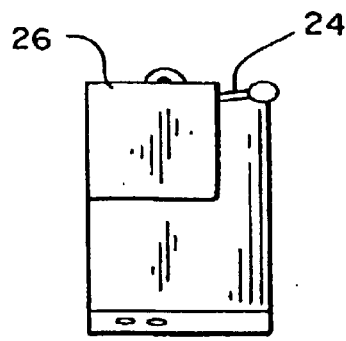

FIGS. 2a–2c represent a system 20 for use as described herein. The system 20 includes a computer processing unit ("CPU") 22, articulating arm 24 connecting a monitor 26 to the system 20, a monitor 26, an acoustical generator 28, and transducer input port 32. In a preferred embodiment, the system 20 can be rolled on rollers 30 to the operating room. In another preferred embodiment, the articulating arm 24 allows for a complete 360 degree rotation and height adjustment by the surgeon.

Figure 3:
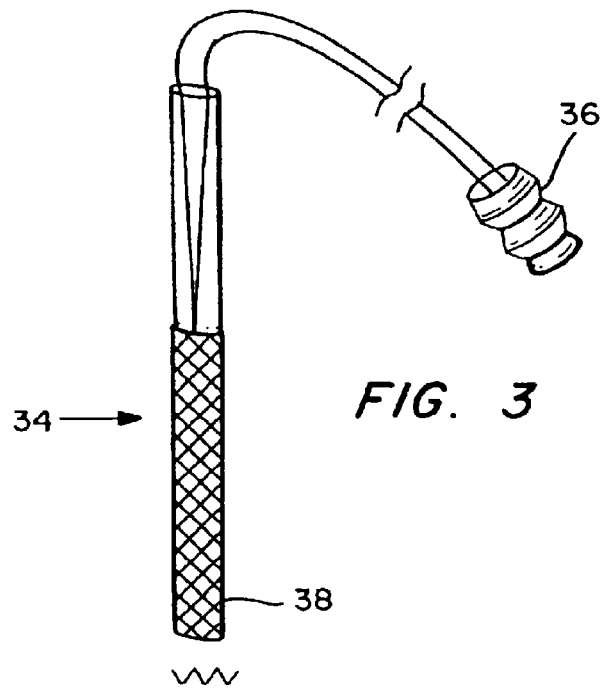
FIG. 3 is a perspective view of a transducer.
Figure 4:
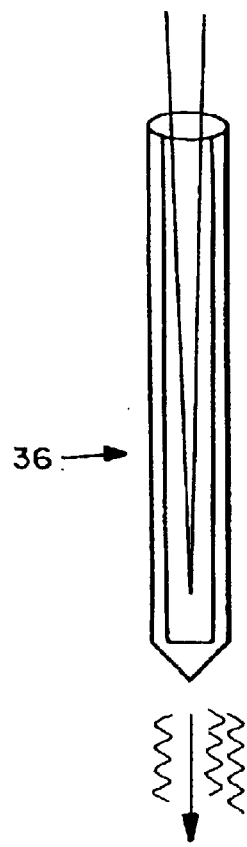
FIG. 4 is a perspective view of input means from the transducer to the transducer input port.

The transducer 34 is shown in more detail in FIG. 3. The transducer 34 includes input and output connections 36 and a probe 38, typically between about 2 and 4 mm in diameter. The transducer emits signals at a defined bandwidth and frequency which is conveyed to and from the input/output connections 36 to the system 20 via the input port 32.

Figure 5B:
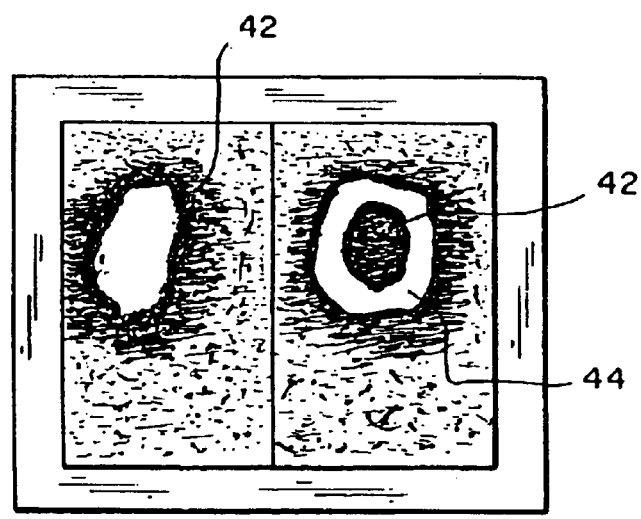
FIGS. 5a and 5b are schematics of the process, wherein the computer processor processes the input and output from the acoustical generator and transducer in FIG. 5a, to produce an image, shown in FIG. 5b.
Figure 5A:
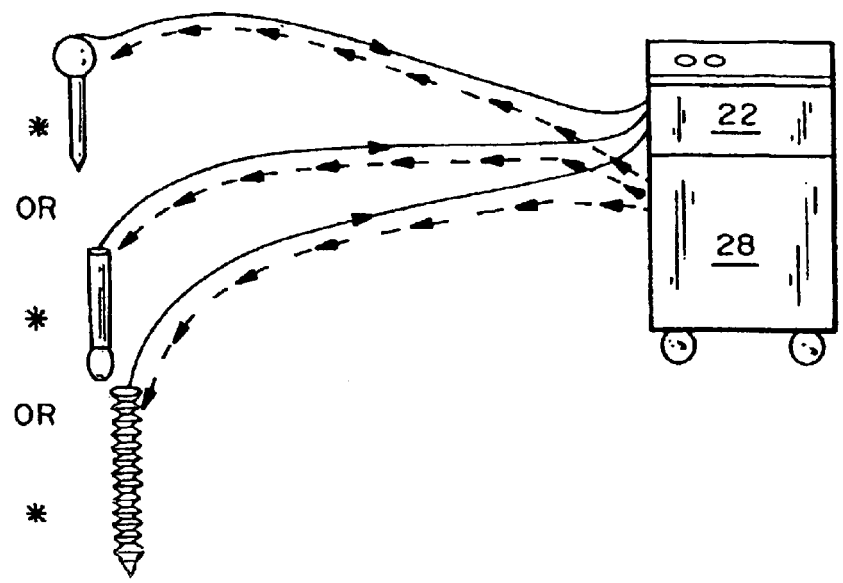

The signals are processed by the CPU 22 to generate signals (FIG. 5a) sent to the monitor 26, which then displays an image of the tissue the probe 38 is passing through. The image 40, shown in FIG. 5b, indicates the cortical interface as a black area 42, and the cancellous tissue as a white area 44. Both radial and sagittal scans can be used to image the tissue, and to provide measurements in real time of the tissue being imaged.

Figures 6A, 6B:
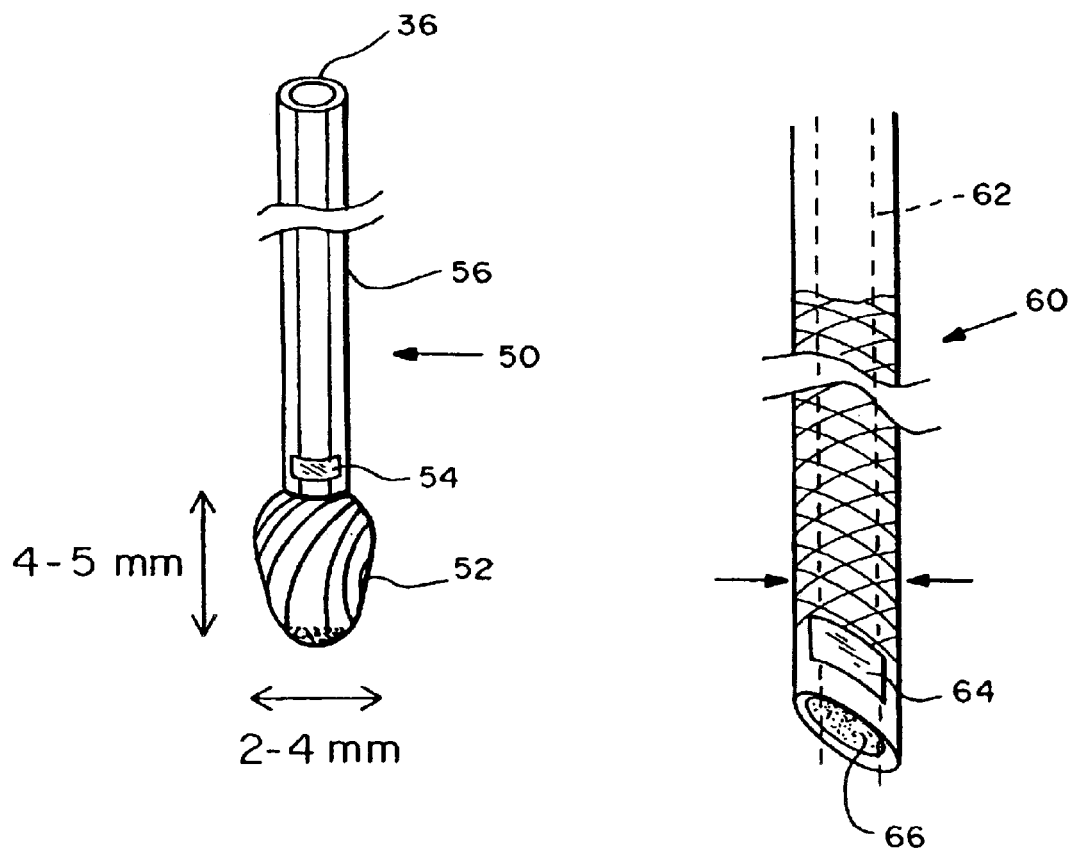

Two general types of instruments can be used to create the images and pilot holes for the surgeon. These consist of instruments such as the drill bits currently in use, modified to include a transducer, as shown in FIGS. 6a and 6b, and instruments wherein the transducer includes a means of creating the pilot hole, as shown in FIGS. 6c and 6d. The latter may be made by modifying existing ultrasound probes to include a hard pointed end. FIG. 6a shows a hollow drill bit 50, with a burr 52 for creating the hole, typically 4–5 mm in height and about 2–4 mm in diameter, a side scan port 54, a lumen 56, and end for connection to the input/output means 36. FIG. 6b shows a hollow drill bit 60, through which the transducer 38 can be introduced through the hollow lumen 62, and visualize the area through side port 64 or forward slot 66.

FIG. 6c shows a "joystick" type of instrument 70. The diameter 72 is between 4 and 8 mm, typically, with an interior lumen diameter 74 of between 2 and 4 mm. There is a side scan port 76 and forward view port 78. A handle 80 directs the drill 82 through the lumen to create the pilot hole in the bone.

FIG. 6d shows a transducer 84 for use in scanning and drilling a pilot hole. The drill bit 86 is about 2–7 mm in diameter. The input/output means 88 connects to port 90.

IOUS can be used to determine the initial starting location that is optimal for introduction of an implant. For example, the transducer is placed on the lamina and used to detect and characterize the bone interface where the implant is to be positioned.

IOUS can be used to navigate through the bone as the surgeon prepares the site for implantation, detecting changes from cortical to cancellous to cartilaginous areas, detecting bone to bone unions, and more clearly defining the area in which the implant is to be placed. For example, IOUS can be used to guide the placement of screws during guidance of pedicle screws across a vertebral body during spinal fusion or during anterior spinal deformity corrective surgery.

Further, IOUS can be used as a diagnostic, for measurement of bone thickness, identification and confirmation of pseudoarthrosis in failed spinal fusions, detection of bone-to-avascular-necrosis interface, detection of fractures, and search for neoplasms, osteoid osteoma and vascular lesions such as aneurismal bone cysts, etc. In general the same equipment and analytical techniques will be used as for surgical placement.

I claim:

1. A method of measuring bore characteristics comprising
   introducing into a region inside of a bone a transducer and receiver for ultrasound or audio signals, and
   monitoring differences in acoustical impedance as the transducer and receiver are moved through the region.

2. The method of claim 1 wherein the bone characteristic is thickness.

3. The method of claim 1 wherein the bone characteristic is identification and confirmation of pseudoarthrosis in failed spinal fusions.

4. The method of claim 1 wherein the bone characteristic is bone-to-avascular-necrosis interface.

5. The method of claim 1 wherein the bone characteristic is an osteoid osteoma or vascular lesion.

6. The method of claim 5 wherein the vascular lesion is an aneurismal bone cyst.

* * * * *